US010738902B2

(12) United States Patent
Waldron (10) Patent No.: US 10,738,902 B2
(45) Date of Patent: Aug. 11, 2020

(54) METHODS, DEVICES AND SYSTEMS FOR A VALVE-CONTACTING ASSEMBLY (71) Applicant: Joseph M. Waldron, Gainesville, FL (US)

(72) Inventor: Joseph M. Waldron, Gainesville, FL (US)

(*) Notice: Subject to any disclaimer, the term of this patent is extended or adjusted under 35 U.S.C. 154(b) by 124 days.

(21) Appl. No.: 15/843,600

(22) Filed: Dec. 15, 2017

(65) Prior Publication Data
US 2018/0172168 A1 Jun. 21, 2018

Related U.S. Application Data (60) Provisional application No. 62/436,281, filed on Dec. 19, 2016.

(51) Int. Cl.
F16K 15/20 (2006.01)
B65B 31/04 (2006.01)
B65D 81/20 (2006.01)
B65D 81/05 (2006.01)
A61M 39/26 (2006.01)
A61J 1/20 (2006.01)

(52) U.S. Cl.
CPC ........... F16K 15/202 (2013.01); A61J 1/2096 (2013.01); A61M 39/26 (2013.01); B65B 31/047 (2013.01); B65D 81/052 (2013.01); B65D 81/2038 (2013.01); F16K 15/20 (2013.01); Y10T 137/3584 (2015.04); Y10T 137/3724 (2015.04); Y10T 137/6137 (2015.04)

(58) Field of Classification Search
CPC .. B65B 31/047; B65D 81/052; B65D 31/147; F16K 15/20; F16K 15/202; Y10T 137/3584; Y10T 137/3724; Y10T 137/6137; A61M 39/26; A61J 1/2096
See application file for complete search history.

(56) References Cited

U.S. PATENT DOCUMENTS

| 3,986,508 | A | * | 10/1976 | Barrington | ................. A61L 2/00 604/411 |
| 4,114,230 | A | * | 9/1978 | MacFarland | ............... A47L 7/04 137/223 |
| 5,064,416 | A | * | 11/1991 | Newgard | ............ A61M 39/045 251/149.1 |
| 5,135,489 | A | * | 8/1992 | Jepson | ................... A61J 1/2089 600/578 |
| 6,871,679 | B2 | * | 3/2005 | Last | .................... B65D 75/5877 137/614.05 |
| 7,232,419 | B2 | * | 6/2007 | Castellanos | ............. A61M 1/28 206/438 |
| 2003/0015452 | A1 | * | 1/2003 | Su | ....................... B65D 81/2038 206/524.8 |
| 2012/0104054 | A1 | * | 5/2012 | Terwilliger | ............ A61J 1/1437 222/563 |
| 2015/0297830 | A1 | * | 10/2015 | Okiyama | ............... A61M 5/162 604/250 |

* cited by examiner

Primary Examiner — Atif H Chaudry
(74) Attorney, Agent, or Firm — Morris, Manning & Martin, LLP; Daniel E. Sineway, Esq.

(57) ABSTRACT

Disclosed are methods, systems and devices for evacuation of fluid, for example, air or gas, from a container or enclosed area.

20 Claims, 4 Drawing Sheets

METHODS, DEVICES AND SYSTEMS FOR A VALVE-CONTACTING ASSEMBLY

RELATED APPLICATION

This application claims the benefit of and priority of U.S. Provisional Patent Application No. 62/436,281, filed Dec. 19, 2016, which is herein incorporated in its entirety.

FIELD OF THE INVENTION

Disclosed herein are methods, devices and systems for a valve-contacting assembly, and optionally comprising a hose, that are useful for inserting or removing air into a container or enclosed area, or for adhering one surface to another with a vacuum, thus creating an enclosed area.

BACKGROUND

It is often desirable to remove the air or gas from a container or enclosed space, for example, when packing and storing materials in a flexible container to remove the air or gas from within the packing containers or bags to reduce the overall size of the packed container. Often, the size of a packed container can be reduced by reducing or eliminating the amount of ambient air or other gases within the container or bag. It may also be desirable to remove the ambient air or other gases from containers in order to preserve the integrity or freshness of the packed materials. Conversely, it may be desirable to inflate containers, for example bags, with ambient air or other gases.

A vacuum seal, whether strong or weak, is one way to attach one structure to another structure without the use of adhesives, or the need for other attachment members that require holes in one or both of the structures, such as screws and bolts.

What is needed are methods, devices and systems for injecting or removing air or other gases from containers or enclosed areas that comprise valves and valve-contacting assemblies for operating the valves to remove or inject the air or gas. What is also needed are methods and devices for use in affixing a one structure to another with a vacuum seal.

BRIEF SUMMARY

Disclosed are devices, methods and systems that allow for evacuating or injecting air or a gas into a variety of containers or enclosed spaces by use of a valve-contacting assembly and optionally, a hose. Additionally, devices, methods and systems can be used with containers such as disposable plastic wear or various storage bags with vacuum packing capabilities or inflation with various gases or ambient air. Valves that may be useful in the present invention are disclosed in U.S. Pat. Nos. 7,895,815; 7,765,777. 7,325,381; and 7,328,548, each of which is incorporated herein in its entirety. An enclosed space may be created by placing a planar or curved structure comprising one or more valves ("a valved structure") over a surface so that an enclosed space is created between the valved structure and the surface. Removing the air in the enclosed space via the valve(s) in the valved structure causes a vacuum to seal or affix the valved structure to the surface.

Disclosed are devices for interacting with a valve to connect the valve to an evacuation device for moving air into or out of a container or enclosed area, such as a pump. In an aspect, an assembly for contacting a valve for evacuating fluid from a container or enclosed area, comprises a valve-interacting unit, comprising a hollow body, with a wall having an interior surface, that defines a recess at a proximal end, and a closed distal end comprising a centrally placed opening in the closed distal end; a probe comprising a hollow tube, having a proximal end and a distal end, that extends through the centrally placed opening of the hollow body, having its distal end protruding through the centrally placed opening and above the closed distal end of the hollow body and having the proximal end of the probe centrally located with the recess, wherein the proximal end of the probe is closed, with one or more openings in the tube in close proximity to the proximal end, and wherein the distal end is configured for fluid connection to a hose or evacuation apparatus; and a deformable member comprising a central channel, wherein the deformable member is disposed within and contacts the interior surface of the hollow body and fills a portion of the recess of the hollow body, thereby defining a surface having a centrally disposed opening therein across the proximal end of the recess, wherein the probe is disposed within the central channel in manner to fill the central channel; wherein when the deformable member is deformed in a direction towards the distal end of the hollow body, the proximal end and the openings of the probe extend beyond the deformable member. In an aspect, an assembly further comprises a hose having a proximal end and a distal end, wherein the distal end of the hose comprises a hose connection area for operatively connecting the hose to an evacuation apparatus, and wherein the proximal end of the hose comprises a hose connection for operatively connecting the distal end of the probe for fluid connection with the probe. In an aspect, the assembly may comprise a cover comprising an opening so that the cover extends over the exterior of the distal end of the hollow body and encloses the distal end of the hollow tube. In an aspect, a hose may comprise one or more electrical connectors (e.g., wires) disposed within an interior channel of the hose. Such wires or electrical connectors may be used to connect sensors or deliver commands in a feedback loop system for control of an evacuation apparatus. Such a connection may also be made by other connecting means such as Bluetooth connections. In an aspect, an evacuation apparatus is a vacuum pump, such as an electrically powered vacuum pump. In an aspect, an evacuation apparatus is a hand-held syringe pump comprising a barrel container and plunger.

Disclosed are methods and systems for using an assembly disclosed herein. In an aspect, a method of using an assembly comprises contacting a portion of a valve on the exterior of a container or enclosed area, wherein a portion of the valve is on an exterior surface of a container or enclosed area, and wherein a portion of the valve comprises a raised protrusion encircling a central port hole, with an assembly comprising a valve-interacting unit, comprising a hollow body, with a wall having an interior surface, that defines a recess at a proximal end, and a closed distal end comprising a centrally placed opening in the closed distal end; and a probe comprising a hollow tube, having a proximal end and a distal end, that extends through the centrally placed opening of the hollow body, having its distal end protruding through the centrally placed opening and above the closed distal end of the hollow body and having the proximal end of the probe centrally located with the recess, wherein the proximal end of the probe is closed, with one or more openings in the tube in close proximity to the proximal end, and wherein the distal end is configured for fluid connection to a hose or evacuation apparatus; and a deformable member comprising a central channel, wherein the deformable member is disposed within and contacts the interior surface of the hollow body and fills a portion of the recess of the hollow body, thereby defining a surface having a centrally disposed opening therein across the proximal end of the recess, wherein the probe is disposed within the central channel in manner to fill the central channel; wherein when the deformable member is deformed in a direction towards the distal end of the hollow body, the proximal end and the openings of the probe extend beyond the deformable member. In an aspect, an assembly further comprises a hose having a proximal end and a distal end, wherein the distal end of the hose comprises a hose connection area for operatively connecting the hose to an evacuation apparatus, and wherein the proximal end of the hose comprises a hose connection for operatively connecting the distal end of the probe for fluid connection with the probe. Contacting the raised protrusion of the portion of the valve on the exterior of the container or enclosed area moves the deformable member in a distal direction and the proximal end of the probe protrudes through the central port hole of the valve and into the container or enclosed area, so that the interior of the container or enclosed areas and the probe are in fluid connection; and the surface of the deformable member is contacting the protrusion of the valve cap to form an air-tight seal. Further steps of a method may comprise, in no particular order, connecting the distal end of the probe to an evacuation apparatus or optionally, connecting the proximal end of the hose to the distal end of the probe and connecting the distal end of the hose to an evacuation apparatus. Once the connections are made, the evacuation apparatus is activated so that fluid is moved from the interior of the container or enclosed area by the evacuation apparatus. In an aspect, the fluid may be air or a gas. In an aspect, the evacuation apparatus is a vacuum pump. In an aspect, the evacuation apparatus is a hand-held syringe comprising a barrel container and plunger.

Additional advantages of the disclosed methods, devices and systems will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed methods, devices and systems, and together with the description, serve to explain the principles of the disclosed methods, devices and systems.

DETAILED DESCRIPTION

The disclosed devices, methods and systems may be understood more readily by reference to the following detailed description of particular embodiments and Examples included therein and to the Figures and their previous and following descriptions.

It is understood that the disclosed devices, methods and systems are not limited to the particular methodology or components described as these may vary. It is also to be understood that the terminology used herein is for the purpose of describing particular embodiments only, and is not intended to limit the scope of the present invention which will be limited only by the appended claims.

Disclosed are devices, methods and systems for evacuating or injecting air or gas into a container or enclosed area. Disclosed devices, methods and systems are useful for controlling the amount of air within a container or an enclosed area by contacting a valve associated with a container or enclosed area. This can include the evacuation or injection into a container or enclosed area of ambient air or other gases (herein referred to as "air"), including but not limited to oxygen, carbon dioxide, carbon monoxide, argon, hydrogen, nitrogen, fluorine, chlorine, helium, neon, methane, nitrous oxide, and other known gases. Disclosed devices, methods and systems are useful with valves in almost any type of container or enclosed area. For example, valves in containers of thin plastic with firm walls or lids can be utilized with disclosed devices, methods and systems, for example, but not limited to, Ziploc® or Glad® brand storage containers.

Disclosed devices, methods and systems are useful with valves in air-tight bag-like containers comprising relatively thin, flexible material, including, but not limited to, plastic, rubber, fabric, paper, self-sealing storage bags. When sealed, these types of storage bags create an air-tight chamber. When a disclosed device of the subject invention interacts with a valve in such a bag, air can be evacuated to create a vacuum or partial vacuum within the bag. Conversely, disclosed devices can also allow air to be injected into a bag, container or enclosed area.

An enclosed area may be formed, for example, by the interaction of a surface of a structure with a valve therein with another structure, e.g., container or a containable area, that when operatively in contact, the two structures together define a cavity, an enclosed area. Herein, a containable area is an open-ended cavity defined by a structure such that when another structure contacts the opening of the cavity, the cavity is no longer open-ended, but is closed. An example is an open container, the open-ended cavity, which is then closed with a lid (the other structure) over the open end of the container. Herein, the surface with a valve therein may be referred to as a first surface for clarity. For example, the first surface may have a valve within and traversing the surface, so that when the first structure is contacted to a container or containable area and thus defines an enclosed area, the valve may be used to create at least a partial vacuum in the enclosed area so that the first surface is held in place (by the vacuum) against the container or the structure defining the containable area. For example, a first surface may be a lid and the lid may have a valve located within and traversing it, and when the lid is placed on a container, an enclosed area is formed. A vacuum may be created in the enclosed area when a valve, located in the surface or in the lid, is used to remove the fluid (e.g., air) trapped within the cavity defined by the container and the lid. The lid and the container are then held together without the need for attachment elements such as bolts, screws, clamps, etc., to hold the container to the lid to define an enclosed space. The lid may have any shape that can interact with the container or containable space so as to define an enclosed cavity and to sufficiently seal closed the enclosed area so that the lid remains in place with the container or containable space while the vacuum exists between them.

Disclosed devices and systems in general, comprise a valve-contacting assembly for interacting with a valve, and optionally a hose, to open the valve and connect the interior of the container or enclosed area to an evacuation apparatus, such as a pump or syringe. Exemplary devices and systems are disclosed in the Figures. For brevity, a valve in a container is disclosed, wherein it is understood that the valve can also be in a lid, a wall or any structure (surface) of an enclosed area, and the disclosure is not limited to containers.

Figure 1A:
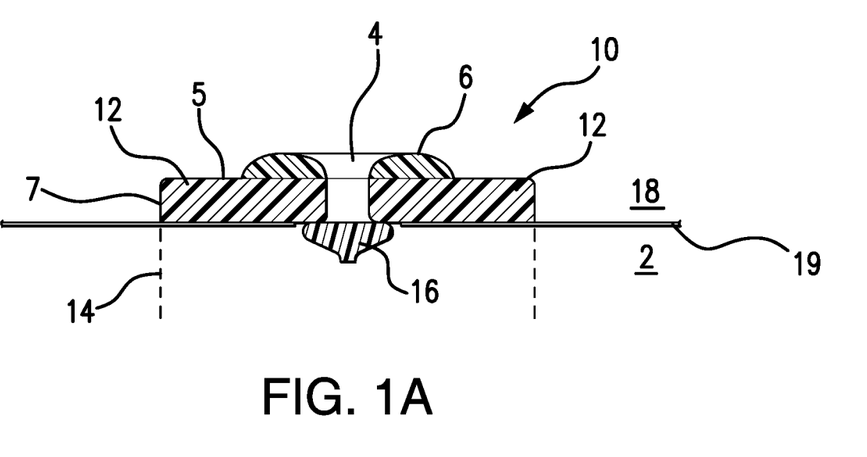
FIG. 1A is a cross-section view of an exemplary valve that can be used with disclosed methods, devices and systems.

FIG. 1A shows a cross-section view of an exemplary valve wherein wall 19 of a container (not shown) separates the interior 2 of the container from the exterior 18. Valve 10 has cap 12 on the exterior of the container and base 14 on the interior of the container, and plug 16, such that when valve 10 is closed, plug 16 is in place and closing port 4. Port 4 is generally circular, though it can be any shape, and is formed by an opening in and through cap 12 (see FIG. 1B, a top view of valve 10). The shape of cap 12 is not limited to an annular shape as shown, but can be any shape that can interact with a valve-contacting assembly. As shown, cap 12 has side edge 7, which is formed by a wall perpendicular to the exterior top surface 5. Raised section 6 may or may not be present on a valve. Raised section 6 may be provided on a valve to allow for closer contact with the valve-contacting assembly deformable member. Side edge 7 is shown as perpendicular to the surface of container surface 19, though the side edge may have other functional shapes. In an aspect, a valve for use with the disclosed valve assembly may be a one-way check valve that permits the withdrawal of air from within the container, but prevents air from re-entering the container from the outside.

Figure 1B:
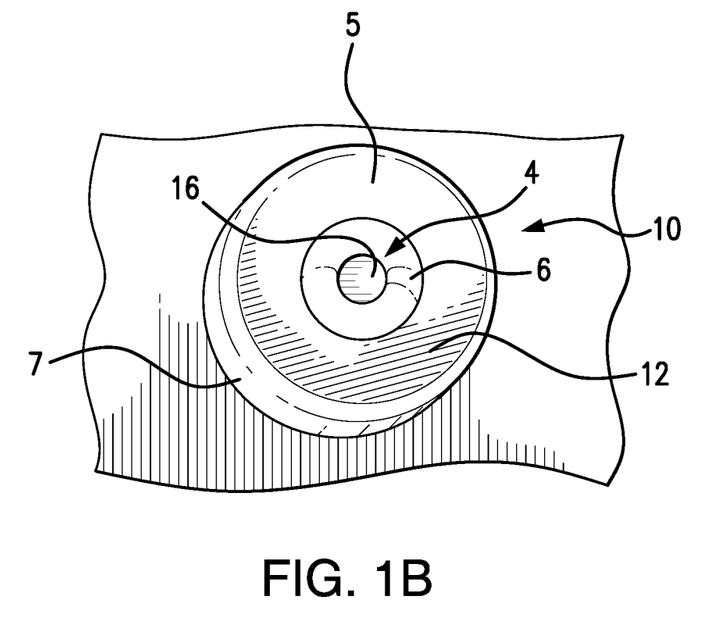
FIG. 1B is a top view of the exemplary valve of FIG. 1A.
Figure 2A:
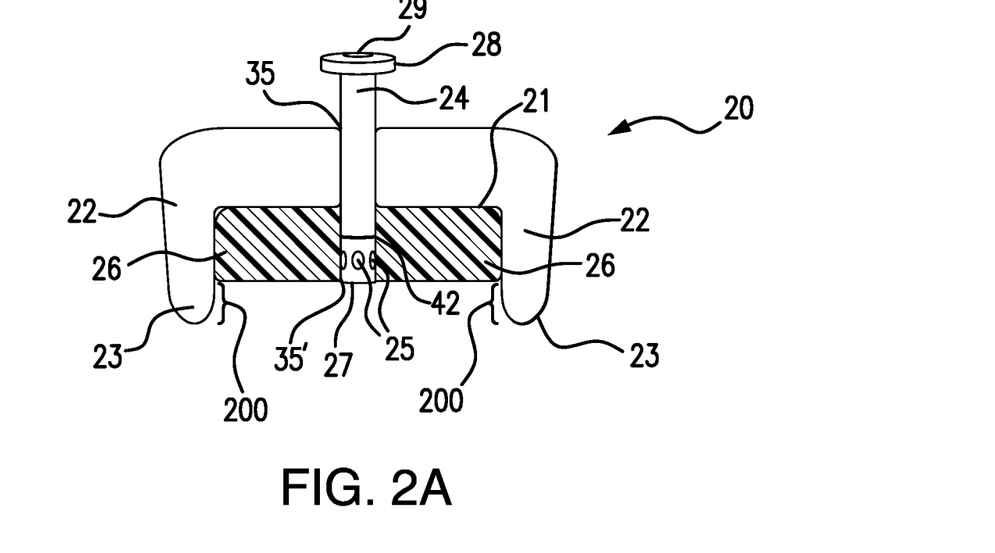
FIG. 2A is a cross-section view of an exemplary valve-contacting assembly.

FIG. 1B shows a top view of an exemplary valve 10, for example, located on the exterior of a container (not shown but indicated in FIG. 1B). Valve 10 comprises cap 12 with walls forming port 4 which is closed by plug 16 which is located on the interior of the container. Raised section 6 may or may not be present. A portion of side edge 7 is shown FIG. 2A shows a cross-section of an exemplary disclosed valve-contacting assembly, wherein probe 24 and its components, and optional O ring 42 not shown in cross-section. Valve-contacting assembly 20 comprises a hollow body 22 having closed end 21 and open end 23, wherein the wall of closed end 21 has an opening 35 therethrough. Opening 35 may or may not be located along the center axis in closed end 21. In an aspect, residing within opening 35 is probe 24. Probe 24 is a hollow tube that is open on its distal end 29. Probe 24 comprises an attachment element 28 proximal to or forming a portion of its distal end 29. In an aspect, on its proximal end, probe 24 has a closed end 27, and in a distal direction from, and proximate to, closed end 27 are lateral openings 25 formed therethrough the wall of probe 24 so that a fluid (e.g., air) can traverse from the interior of probe 24 through openings 25 to outside of probe 24, or from the area exterior to probe 24 through openings 25 into the interior of probe 24. Disclosed alternate probes may have differently shaped proximal ends. A probe disclosed herein may optionally further comprise O ring 42 on its exterior surface to aid in contact with deformable member 26 or a valve. (See FIGS. 4C and 4D. Deformable member 26 comprises channel 35' which is an open channel formed in deformable member 26. Channel 35' is aligned with opening 35 in hollow body 22, and the aligned channel 35' and opening 35 may be located along the center axis in the valve-contacting assembly or may be displaced from the center axis. In an aspect, disposed within aligned channel 35' and opening 35 is probe 24. Deformable member 26 resides in and substantially, but not completely, fills the interior of hollow body 22 except for perimeter zone 200, located substantially adjacent to open end 23. Deformable member 26 may or may not be attached to the interior surface of closed end 21. In use, perimeter zone 200 may contact an exterior surface of a valve. See FIG. 2B where perimeter zone 200 (not marked) is shown in contact with side edge 7. Perimeter zone 200, comprising the proximal interior surface of the wall of hollow body 22 at open end 23 may have features that aid in its interaction with the exterior portions of a valve, including, but not limited to, snap fit elements, lateral or horizontal ribs protruding into the interior, or an inwardly or outwardly tapered surface, for forming a sufficiently tight junction with the exterior of a valve, such as a side surface of a valve.

Deformable member 26 resides within the interior cavity defined by hollow body 22. When contacted, such as by a valve surface, deformable member 26 is compressed such that it fills the interior of hollow body 22 and forms a seal against the contacting surface (e.g., the valve surface). In its compressed state, for example, when in contact with a valve, deformable member 26 prevents fluid flow or leakage in the interior of hollow body 22 and at the intersection of the exterior of probe 24 and the valve opening.

Deformable member 26 may be made of a material that is fluid impermeable, such as air impermeable. In an aspect, the material is flexible and capable of being compressed. Deformable member 26 may be made of one or more materials that can provide it with physical properties of flexibility, compressibility and substantial imperviousness to a fluid, such as air. In an aspect, a deformable member, when it is not under compression, maintains its shape, and when compression conditions cease, the deformable member returns to substantially its original shape. In an aspect, the deformable member is resistant to permanent deformation caused by applied pressure. In an aspect, a deformable member is pliable so that when compressed against a surface, the deformable member conforms to the contours of that surface. In an aspect, a deformable member is relatively impervious to air.

A deformable member may comprise one or more materials and could consist of a core surrounded by a coat, of which the core and coat may be made of the same or different materials and/or chemical compounds and or molecules. The same chemical compound/molecule may be used for the core and the coat, but the chemical compound/molecule may be made more dense or less dense by, for example, chemical or physical means, For example, a core of a deformable member may be made from a more dense form of the chemical compound/molecule and the coating is made from a less dense form of the same chemical compound/molecule. For example, a polymeric chemical compound/molecule may be made more dense by for example, cross-linking the polymers, and a less dense form of the same polymeric chemical compound/molecule may have a lower amount of cross-linking. In an aspect, a deformable member may be made from two or more different chemical compounds/molecules.

In an aspect, a deformable member may be made of medical grade materials. In an aspect, a deformable member may comprise ethyl vinyl acetate. In an aspect, a deformable member may comprise silicone. Those of skill in the art can determine materials that can be used to make deformable members that function in the devices disclosed herein.

Figure 2B:
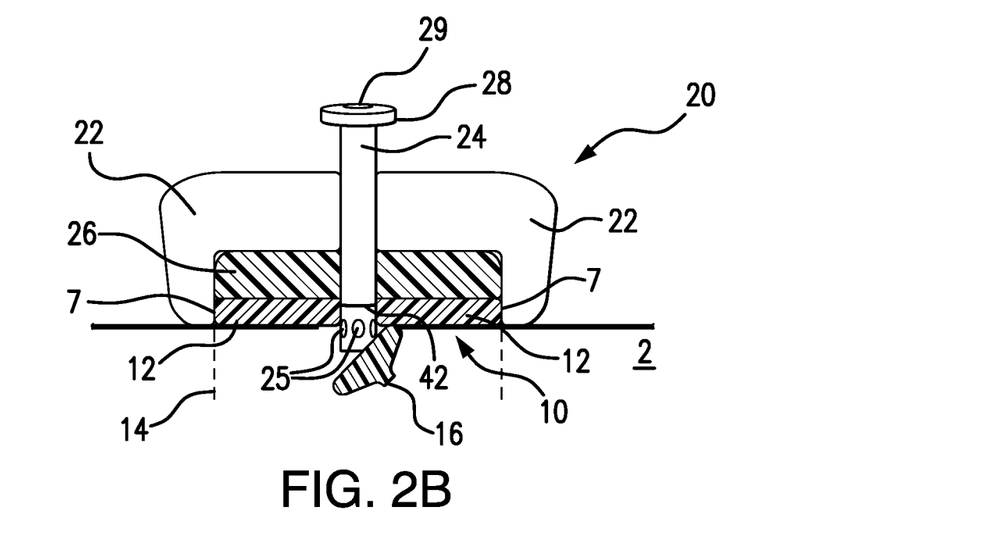
FIG. 2B shows a cross-section view of an exemplary valve-contacting assembly in contact with a valve.

FIG. 2B shows an exemplary valve-contacting assembly 20 in contact with and opening valve 10, which includes base 14. Deformable member 26 is compressed by contacting cap 12 when hollow body 22 is contacted with valve 10. Perimeter zone 200 (not shown) is contacting side edge 7 of valve 10. Probe 24 is shown comprising distal end 29 and attachment element 28. Probe 24 has been moved through port 4 (not shown) of valve 10 and has displaced cap 16. Optionally, an O ring 42 which is located on the exterior of probe 24 resides between the exterior of probe 24 and the surface of port 4 to form a fluid (e.g. air) tight seal. For example, openings 25 are now located within interior 2 so that there is a fluid connection between interior 2 and at least the interior of probe 24.

Figure 3A:
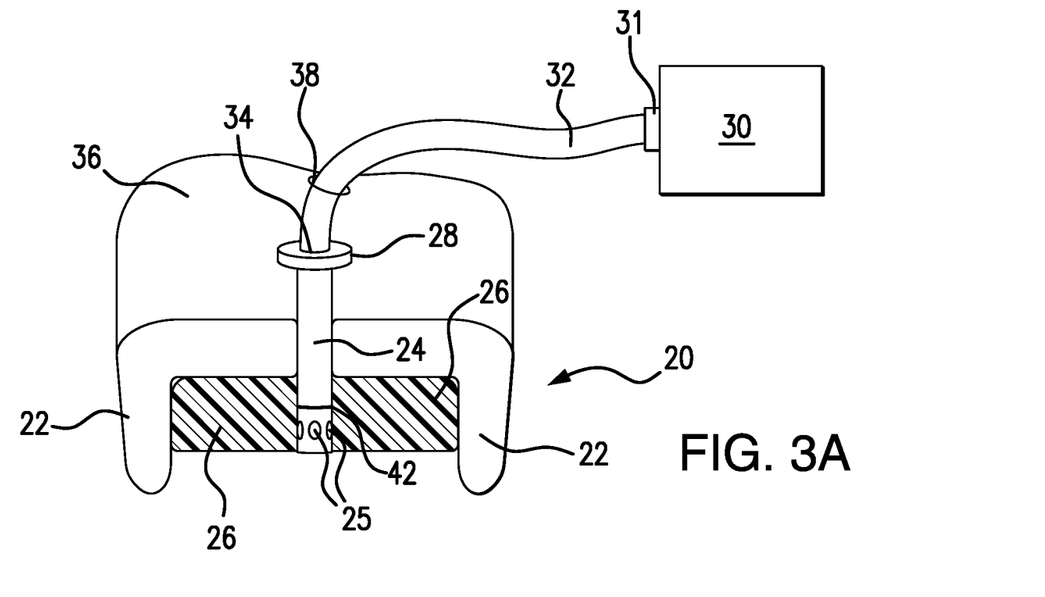
FIG. 3A shows a cross-section view of an exemplary valve-contacting assembly with a cover, an attached hose and an evacuation apparatus.

FIG. 3A shows a cross-section of valve-contacting assembly 20 with cover 36, wherein probe 24 and its components, and including hose attachments 34 and 31, O ring 42, hose 32, and evacuation apparatus 30 are not shown in cross-section. Cover 36 defines opening 38 through which hose 32 can traverse. Hose 32 attaches to probe 24 by attachment element 28 of probe 24 interacting with hose attachment element 34. O ring 42 is shown on the exterior of probe 24. Attachment elements, such as attachment element 28 and hose attachment element 34, can be paired such that one offers a receiving connection element and the other offers an insertion connection element, or can be other known elements such as snap-fit, luer lock, clamp, screw, or other attachment elements known to those of skill in the art. Hose 32 has attachment element 31 on its distal end for attaching to evacuation apparatus 30. Attachment of hose 32 on its distal end by attachment element 31 to evacuation apparatus 30 or other evacuation apparatus such as evacuation apparatus 30' (a syringe, see FIG. 3B) and on its proximal end via attachment element 28 to probe 24 allows for fluid connection between evacuation apparatus 30 (or for example, 30') and the interior of a container or containable area when probe 24 engages with a valve to open the valve and position openings 25 (or alternatively opening 27', see FIG. 4B) within the container or containable area comprising the valve. Cover 36 may be removable from valve-contacting assembly 20. Cover 36 forms a covering over the distal exterior of hollow body 22 and may be of any shape. Cover 36 may contact any portion of hollow body 22, for example, a distal perimeter area of hollow body 22. Contact between cover 36 and hollow body 22 may be maintained by elements such as snap-fit, mirrored inclined surfaces, by tight association of the surfaces of cover 36 and hollow body 22, screw threads, clips, and other known elements for maintaining contact between two objects.

Hose 32 may have wires or electrically conductive material disposed on the interior surface for electrical connection with evacuation apparatus 30 (such wires or material are not shown). If such wires or material is present, attachment elements, e.g., 28 and 31, may also include electrical connections such that electrical connection is made between evacuation apparatus 30 and at least the hose, where sensors or control units for the operation of the evacuation unit may be located. It is well known in the art to utilize electrical wires along the length of a hose or other tubing in order to provide a source of electrical current along the length of the hose or tubing and/or to the end of the hose or tubing. It is also well known in the art to control electrical current with any of a variety of switches, which may be located at the evacuation apparatus or on the hose. For example, a fluid pressure sensor (e.g., an air pressure sensor) located at the proximal end of the hose may be activated when a particular pressure is reached in the proximal end of the hose during activation of the evacuation apparatus. When the desired pressure is reached, the sensor is activated to send a signal to the evacuation apparatus. For example, the signal may then deactivate (turn off) the evacuation apparatus.

Figure 3B:
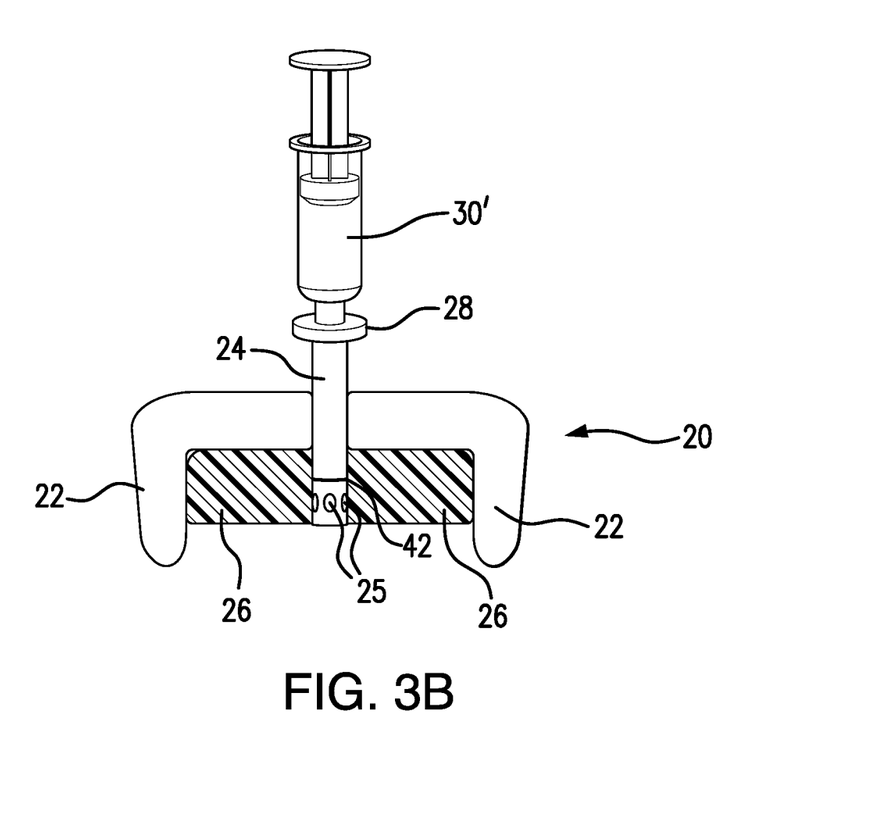
FIG. 3B shows a cross-section view of an exemplary valve-contacting assembly and an attached evacuation apparatus.

FIG. 3B shows a cross-section view of valve-contacting assembly 20, wherein probe 24 and its components, O ring 42, and evacuation apparatus 30' are not shown in cross-section. Cover 36 is not shown, but could be present. Hose 32 is not shown but could attach to probe 24 by attachment element 28 of probe 24 interacting with hose attachment element 34. Attachment elements, such as attachment element 28 and hose attachment element 34, can be paired such that one offers a receiving connection element and the other offers an insertion connection element, or can be other known elements such as snap-fit, luer lock, clamp, screw, or other attachment elements known to those of skill in the art. Hose 32, having attachment element on its distal end, can attach to evacuation apparatus 30'. Attachment of hose 32 on its distal end by attachment element 31 to evacuation apparatus 30' (a syringe) or other evacuation apparatus such as evacuation apparatus 30, and on its proximal end via attachment element 28 to probe 24 allows for fluid connection between evacuation apparatus 30' (or for example, 30) and the interior of a container or containable area when probe 24 engages with a valve to open the valve and position openings 25 (or alternatively opening 27', see FIG. 4B) within the container or containable area comprising the valve. In FIG. 3B, evacuation apparatus 30' is directly attached to attachment element 28 of probe 24 through an attachment element of evacuation apparatus 30', such attachment elements can be paired such that one offers a receiving connection element and the other offers an insertion connection element, or can be other known elements such as snap-fit, luer lock, clamp, screw, or other attachment elements known to those of skill in the art. As shown, evacuation apparatus 30' is a hand-held syringe, for which a luer lock attachment element to connect probe 24 and evacuation apparatus 30' would be known to those of skill in the art. Other features are common between FIG. 3A and FIG. 3B, for valve-contacting assembly, including probe 24 with openings 25, optional O ring 42 on probe 24, hollow body 22, and deformable member 26.

Figure 4A:
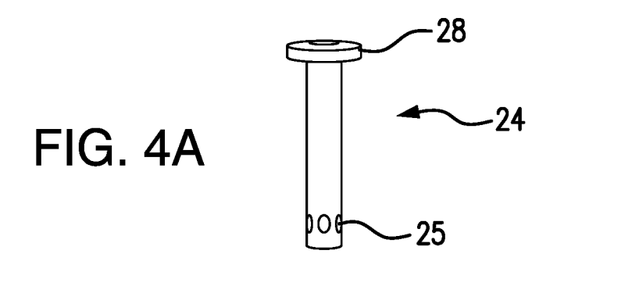
FIG. 4A shows an exemplary probe having a closed end and lateral openings adjacent to the closed end.
Figure 4B:
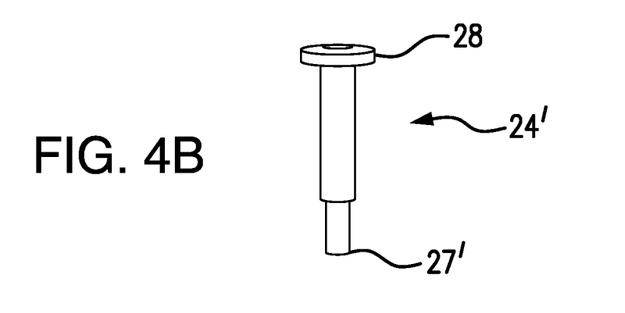
FIG. 4B shows an exemplary probe having an open end.
Figure 4C:
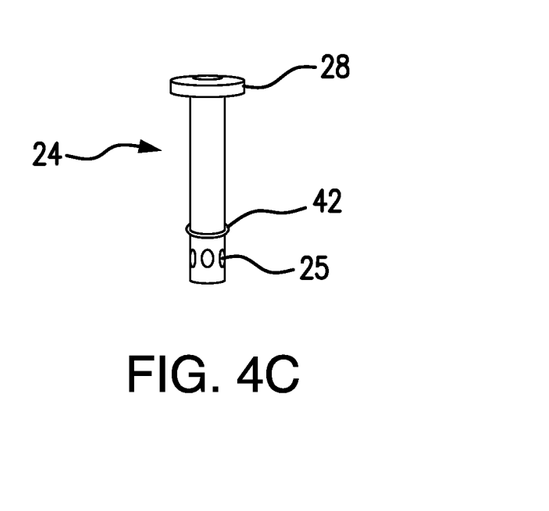
FIGS. 4C and 4D show the exemplary probe of FIGS. 4A and 4B further comprising an O ring.
Figure 4D:
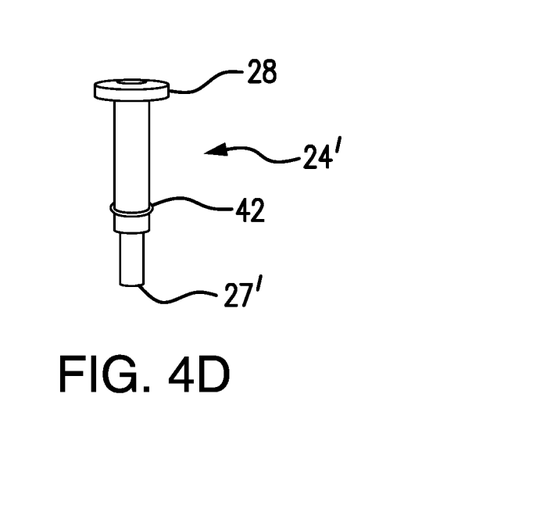

FIG. 4A shows a view of exemplary probe 24, with lateral openings 25 and attachment element 28. Attachment element 28 is formed so that other elements, such as a hose or a syringe, can be attached and in fluid connection with the interior of the probe and when in use, through the valve to the interior of the container. FIG. 4B shows an alternative probe 24' wherein a portion of the proximal end of the probe is narrowed and proximal end 27' of the probe is not closed, but open, so that when in use with a valve on a container or a containable area, probe 24 positioned so that proximal end 27, which is open so that the interior of probe 24 is in fluid connection (through the proximal end '27) with the interior of the container. Attachment element 28 is present on probe 24'. FIGS. 4C and 4D show the exemplary probes 24 of FIGS. 4A and 4B, further comprising an optional O ring 42 adjacently positioned near the proximal end of probe 24. The O ring may be fixed at a particular location or may be movable along the length of probe 24. The O ring functions to provide a seal between probe 24 and the interior of a valve's opening, such as the surface of port 4, and thus may be positioned on the exterior of probe 24 so that when the valve-contacting assembly is in contact with a valve and probe 24 enters and transits the valve opening, the O ring is located within the port of the valve to provide a seal.

An evacuation apparatus may further comprise elements for measuring and indicating the amount of fluid, air or gas, moved by the apparatus. For example, an indicator may report the vacuum created by the evacuation apparatus in mbar, atm, torr, microns, psi or in.-Hg, or by change in location of the plunger in a syringe.

Disclosed are methods of using the valve-contacting device disclosed herein. As shown in FIG. 2B, in using valve-contacting device 20 with a valve, such as valve 10, the interior surface of perimeter zone 200 of hollow body 22 slidably contacts side edge 7 of valve 10 in a distal to proximal direction. When the movement of hollow body 22 is complete, such that the interior surface of perimeter zone 200 of hollow body 22 has contacted side edge 7 of valve 10 to a desired extent, such as having open end 23 contact or be adjacent to the container surface, deformable member 26 is pushed in a distal direction so that it substantially fills the interior of hollow body 22, and contacts exterior top surface 5 of cap 12 of valve 10. Contact between deformable member 26 and exterior top surface 5 of cap 12 forms a tight seal that prevents leakage of gas into or out of the valve. Movement of valve-contacting assembly 20 onto valve 10 causes closed end 27 of probe 24 to enter port 4 of valve 10, transit port 4, and displace plug 16 so that lateral openings 25 are within the interior of the container or containable area. Optionally, O ring 42 is positioned between the exterior of probe 24 and valve port 4 to form an additional seal to prevent fluid leakage along the exterior of probe 24. Once lateral openings 25 are within the container, the interior of the container and the interior of probe 24 are in fluid connection. If evacuation apparatus 30 or 30' is attached to the distal end of probe 24 (not shown), evacuation apparatus 30 or 30' is also in fluid connection with the interior of the container or containable area.

Once evacuation apparatus 30 or 30' is in fluid connection with the interior of the container, evacuation apparatus 30 or 30' can be activated to insert or remove fluid, e.g., air or gas, into or out of the container or containable area. Once the desired amount of fluid, e.g., air or gas, has been inserted or removed, evacuation apparatus 30 or 30' is deactivated. Alternatively, sensors, for example, in hose 32 may be activated to turn-off or stop an evacuation apparatus. Valve-contacting assembly 20 is removed from valve 10 by moving valve-contacting assembly 20 in a distal direction (away from the valve) so that closed end 27 of probe 24 no longer resides within port 4 of valve 10. Plug 16 of valve 10 moves to close port 4, so that substantially the amount of air or gas remaining after deactivation of evacuation apparatus 30 or 30' is maintained in the container.

In a method wherein valve-contacting assembly 20 comprises probe 24', as shown in FIG. 4B, in using valve-contacting device 20 comprising probe 24' with a valve, such as valve 10, such as is shown in FIG. 2B, the interior surface of perimeter zone 200 of hollow body 22 slidably contacts side edge 7 of valve 10 in a distal to proximal direction. When the movement of hollow body 22 is complete, such that the interior surface of perimeter zone 200 of hollow body 22 has contacted side edge 7 of valve 10 to a desired extent, such as having open end 23 contact or be adjacent to the container surface, deformable member 26 is pushed in a distal direction so that it substantially fills the interior of hollow body 22, and contacts exterior top surface 5 of cap 12 of valve 10. Contact between deformable member 26 and exterior top surface 5 of cap 12 forms a tight seal that prevents leakage of gas into or out of the valve. Movement of valve-contacting assembly 20 onto valve 10 causes open end 27' of probe 24 to enter port 4 of valve 10, transit port 4, and displace plug 16 so that open end 27' is within the interior of the container. Optionally, O ring 42 is positioned between the exterior of probe 24' and valve port 4 to form an additional seal to prevent fluid leakage along the exterior of probe 24'. Once open end 27' is within the container, the interior of the container and the interior of probe 24 are in fluid connection. If evacuation apparatus 30 or 30' is attached to the distal end of probe 24' (not shown), evacuation apparatus 30 or 30' is also in fluid connection with the interior of the container.

Once evacuation apparatus 30 or 30' is in fluid connection with the interior of the container, evacuation apparatus 30 or 30' can be activated to insert or remove air or gas into or out of the container. Once the desired amount of air or gas has been inserted or removed, evacuation apparatus 30 or 30' is deactivated. Alternatively, sensors, such as in hose 32, may be activated to turn-off or stop an evacuation apparatus. Valve-contacting assembly 20 is removed from valve 10 by moving valve-contacting assembly in a distal direction (away from the valve) so that open end 27' of probe 24' no longer resides within port 4 of valve 10. Plug 16 of valve 10 moves to close port 4, so that substantially the amount of air or gas remaining after deactivation of evacuation apparatus 30 or 30' is maintained in the container.

Disclosed herein are kits that comprise devices disclosed herein that can be used in practicing the methods disclosed herein. The kits can include any disclosed device or combination of devices disclosed herein or that would be understood to be required or beneficial in the practice of the disclosed methods. For example, a kit can include a valve-contacting assembly comprising a cover and a hose. For example, a kit can include a valve-contacting assembly and a hand-held syringe.

The kits can include instructions for using a valve-contacting assembly disclosed herein in the methods disclosed herein.

DEFINITIONS

It must be noted that as used herein and in the appended claims, the singular forms "a", "an", and "the" include plural reference unless the context clearly dictates otherwise.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range—from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

It is to be understood that the disclosed methods, devices and systems are not limited to specific methods or specific components, unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed methods, devices and systems. These and other materials are disclosed herein, and it is understood that when combinations, subsets, etc. of these materials are disclosed that while specific reference of each various individual and collective combinations and permutation of these components may not be explicitly disclosed, each is specifically contemplated and described herein. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and an example combination A-D. This concept applies to all aspects of this application including, but not limited to, steps in methods of making and using the disclosed devices. Thus, if there are a variety of additional steps that can be performed it is understood that each of these additional steps can be performed with any specific embodiment or combination of embodiments of the disclosed methods, and that each such combination is specifically contemplated and should be considered disclosed.

Using a valve-contacting assembly to evacuate air in a container. A food storage container having a container body and lid with a valve such as that shown in FIG. 1A and 1B was used to store vegetables. The lid was engaged with the container to close the container. A valve-contacting assembly (assembly) was used to remove the air from the closed container. The valve-contacting assembly was sized so that perimeter zone 200 engaged the outer side surface of the valve when the assembly and the valve were contacted. As the perimeter zone 200 was sliding onto the valve outer side surface, the probe was entering the valve opening. Concurrently, the deformable member was contacting the valve upper surface and making an air tight seal around the probe and the valve opening. Once the assembly was fully engaged with the valve, the vacuum pump, attached to assembly through a hose, was activated. Air was removed from the closed container, and once the desired amount of air was removed, the pump was deactivated. The assembly was then removed, leaving the valve closed. The storage container was then placed in the refrigerator. Those skilled in the art will recognize, or be able to ascertain using no more than routine experimentation, many equivalents to the specific embodiments of the method and compositions described herein. Such equivalents are intended to be encompassed by the following claims.

What is claimed is:

1. An assembly for contacting a valve for evacuating fluid from a container or enclosed area, comprising:
   a) a valve-interacting unit, comprising
      i) a hollow body comprising a wall having an interior surface that defines an interior cavity having an open proximal end, and a closed distal end comprising a centrally placed opening in the closed distal end;
      ii) a probe comprising a hollow tube, having a proximal end and a distal end, that extends through the centrally placed opening of the hollow body, having its distal end protruding through the centrally placed opening and beyond the closed distal end of the hollow body and having the proximal end of the probe centrally located within the interior cavity, wherein the proximal end of the probe is closed, with one or more openings in the tube in close proximity to the proximal end, and wherein the distal end is configured for fluid connection to a hose or evacuation apparatus;
      iii) a deformable member comprising a central channel, wherein the deformable member is disposed within the interior cavity of the hollow body and fills a portion of the interior cavity of the hollow body, thereby defining a surface having a centrally disposed opening therein across the proximal end of the interior cavity, wherein the probe is disposed within the central channel in manner to fill the central channel;
   b) a valve body comprising a shape configured to fit snugly within the interior cavity of the valve-interacting unit, the valve body including a port with an open proximal end and open distal end, wherein the proximal end of the port is closed by a flexible plug, wherein the valve-interacting unit fits over the valve body so that the probe of the valve-interacting unit slides into the distal end of the port and the deformable member contacts the valve body;

wherein when the deformable member presses onto the valve body, the deformable member is deformed in a direction towards the distal end of the hollow body, causing the deformable member to deform to create a seal around the probe, further causing the proximal end and the openings of the probe to extend beyond the deformable member through the distal end of the port to displace the flexible plug from the proximal end of the port;

wherein when the valve-interacting unit is removed from the valve body, the flexible plug returns to its original position and thereby closes the proximal end of the port; and c) a hose having a proximal end and a distal end, wherein the distal end of the hose comprises a hose connection area for operatively connecting the hose to an evacuation apparatus, and wherein the proximal end of the hose comprises a hose connection for operatively connecting the distal end of the probe for fluid connection with the probe.

2. The assembly of claim 1, further comprising a cover comprising an opening so that the cover extends over the exterior of the distal end of the hollow body and encloses the distal end of the hollow tube.

3. The assembly of claim 1, wherein the hose further comprises one or more electrical wires disposed within an interior channel of the hose.

4. The assembly of claim 1, wherein the interior surface of the proximal end of the hollow body comprises an annular snap-fit comprising one or more ridges protruding perpendicularly from the interior surface into the recess.

5. The assembly of claim 1, wherein the fluid is air.

6. The assembly of claim 1, wherein the evacuation apparatus is a vacuum pump.

7. The assembly of claim 1, wherein the evacuation apparatus is a hand-held syringe pump comprising a barrel container and plunger.

8. A method of using a hose assembly comprising,

A) contacting a valve on a container, wherein a portion of the valve is on an exterior surface of a container or enclosed area, wherein a portion of the valve comprises a raised protrusion encircling a central port hole, wherein the central port hole comprises a port having an open distal end and an open proximal end, wherein the open proximal end of the port is closed by a plug, with an assembly comprising a) a valve-interacting unit, comprising
  i) a hollow body comprising a wall having an interior surface that defines an interior cavity having an open proximal end, and a closed distal end comprising a centrally placed opening in the closed distal end;
  ii) a probe comprising a hollow tube, having a proximal end and a distal end, that extends through the centrally placed opening of the hollow body, having its distal end protruding through the centrally placed opening and beyond the closed distal end of the hollow body and having the proximal end of the probe centrally located within the interior cavity, wherein the proximal end of the probe is closed, with one or more openings in the tube in close proximity to the proximal end, and wherein the distal end is configured for fluid connection to a hose or evacuation apparatus;
  iii) a deformable member comprising a central channel, wherein the deformable member is disposed within the interior cavity of the hollow body and fills a portion of the interior cavity of the hollow body, thereby defining a surface having a centrally disposed opening therein across the proximal end of the interior cavity, wherein the probe is disposed within the central channel in a manner to fill the central channel; wherein when the deformable member is deformed in a direction towards the distal end of the hollow body, the proximal end and the openings of the probe extend beyond the deformable member; and b) a hose having a proximal end and a distal end, wherein the distal end of the hose comprises a hose connection area for operatively connecting the hose to an evacuation apparatus, and wherein the proximal end of the hose comprises a hose connection for operatively connecting the distal end of the probe for fluid connection with the probe;

wherein when the deformable member is moved by contact with the raised protrusion of the valve, the proximal end of the probe protrudes through the central port hole through the distal end of the port and displaces the plug from the proximal end of the port, causing the probe to protrude into the container or enclosed area, so that the interior of the container or enclosed area and the probe are in fluid connection; and wherein the surface of the deformable member is contacting the protrusion of the valve to form an air-tight seal;

B) connecting the distal end of the probe to an evacuation apparatus; and

C) activating the evacuation apparatus so that fluid is moved from the interior of the container or enclosed area by the evacuation apparatus.

9. The method of claim 8, wherein the hose assembly further comprises a cover comprising an opening so that the cover extends over the exterior of the distal end of the hollow body and encloses the proximal end of the hollow tube, and the proximal end of the hose is disposed within the opening of the cover.

10. The method of claim 8, wherein the hose further comprises one or more electrical wires disposed within an interior channel of the hose.

11. The method of claim 8, wherein the interior surface of the proximal end of the hollow body comprises an annular snap-fit comprising one or more ridges protruding perpendicularly from the interior surface into the recess, and the valve and the hose assembly are held together by the snap-fit.

12. The method of claim 8, wherein the fluid is air.

13. The method of claim 8, wherein the evacuation apparatus is a vacuum pump.

14. The method of claim 8, wherein the evacuation apparatus is a hand-held syringe comprising a barrel container and plunger.

15. A system for evacuating fluid from a container or enclosed area, comprising:

a) a valve-interacting unit, comprising
  i) a hollow body comprising a wall having an interior surface that defines an interior cavity having an open proximal end, and a closed distal end comprising a centrally placed opening in the closed distal end;
  ii) a probe comprising a hollow tube, having a proximal end and a distal end, that extends through the centrally placed opening of the hollow body, having its distal end protruding through the centrally placed opening and beyond the closed distal end of the hollow body and having the proximal end of the probe centrally located within the interior cavity, wherein the proximal end of the probe is closed, with one or more openings in the tube in close proximity to the proximal end, and wherein the distal end is configured for fluid connection to a hose or evacuation apparatus; and iii) a deformable member comprising a central channel, wherein the deformable member is disposed within the interior cavity of the hollow body and fills a portion of the interior cavity of the hollow body, thereby defining a surface having a centrally disposed opening therein across the proximal end of the interior cavity, wherein the probe is disposed within the central channel in manner to fill the central channel; and b) a valve body comprising a shape configured to fit snugly within the interior cavity of the valve-interacting unit, the valve body including a port with an open proximal end and open distal end, wherein the proximal end of the port is closed by a flexible plug, wherein the valve-interacting unit fits over the valve body so that the probe of the valve-interacting unit slides into the distal end of the port and the deformable member contacts the valve body;

wherein when the deformable member presses onto the valve body, the deformable member is deformed in a direction towards the distal end of the hollow body, causing the deformable member to deform to create a seal around the probe, further causing the proximal end and the openings of the probe to extend beyond the deformable member through the distal end of the port to displace the flexible plug from the proximal end of the port;

wherein when the valve-interacting unit is removed from the valve body, the flexible plug returns to its original position and thereby closes the proximal end of the port.

16. The system of claim 15, further comprising a cover comprising an opening so that the cover extends over the exterior of the distal end of the hollow body and encloses the distal end of the hollow tube.

17. The system of claim 15, further comprising a hose having a proximal end and a distal end, wherein the distal end of the hose comprises a hose connection area for operatively connecting the hose to an evacuation apparatus, and wherein the proximal end of the hose comprises a hose connection for operatively connecting the distal end of the probe for fluid connection with the probe.

18. The system of claim 15, wherein the hose further comprises one or more electrical wires disposed within an interior channel of the hose.

19. The system of claim 15, further comprising an evacuation apparatus.

20. The system of claim 19, wherein the evacuation apparatus is a vacuum pump or a hand-held syringe pump comprising a barrel container and plunger.

* * * * *